United States Patent [19]

Kobashi et al.

[11] Patent Number: 4,924,017

[45] Date of Patent: May 8, 1990

[54] STANNIC ACID ANHYDRIDE

[75] Inventors: Toshiyuki Kobashi; Hideo Naka, both of Okayama, Japan

[73] Assignee: Japan Exlan Company Limited, Osaka, Japan

[21] Appl. No.: 222,829

[22] Filed: Jul. 22, 1988

[30] Foreign Application Priority Data

Aug. 5, 1987 [JP] Japan ................. 62-197030
Aug. 5, 1987 [JP] Japan ................. 62-197031
Aug. 7, 1987 [JP] Japan ................. 62-198948
Aug. 7, 1987 [JP] Japan ................. 62-198949
Aug. 7, 1987 [JP] Japan ................. 62-198950

[51] Int. Cl.$^5$ ............................................. C07F 7/22
[52] U.S. Cl. .................................................. 556/85
[58] Field of Search ..................................... 556/85

[56] References Cited

U.S. PATENT DOCUMENTS 2,727,917 12/1955 Mack et al. .............. 556/85 X
3,412,117 12/1968 Davies ....................... 556/85
4,222,950  9/1980 Gitlitz ........................ 556/85 X

OTHER PUBLICATIONS

"Chemical Abstracts", vol. 86, #1070889q, 1976.

*Primary Examiner*—Paul F. Shaver
*Attorney, Agent, or Firm*—Wenderoth, Lind & Ponack

[57] ABSTRACT

A stannic acid anhydride represented by the structural formula shown below. When said compound as it is, or the same coated on a substrate or impregnated into it, is baked, it is possible to finally form tin oxide which has excellent transparency and conductivity,

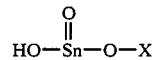

wherein X represents

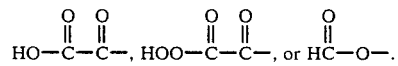

1 Claim, No Drawings

STANNIC ACID ANHYDRIDE

BACKGROUND OF THE INVENTION (a) Field of the Invention

The present invention relates to a stannic acid anhydride suitable for forming transparent conductive tin oxide, and to conductive products covered with tin oxide.

(b) Description of the Prior Art

In recent years, accompanied with the remarkable development in the field of electro-optical elements, attention is paid to transparent conductive films of the type of $SnO_2$ or $In_2O_3$. They are actively developed, for example, as transparent electrodes of various optical devices such as those of electro-luminescence, liquid crystals, image accumulation devices, etc.; as heating elements or resistors utilizing their heat resistance and anti-abrasion properties; as solar cells utilizing their high conductivity; or as selective permeable films for use in solar heat electricity generation utilizing their high reflexibility in infrared rays.

Among the methods of forming these transparent conductive films are known:

(1) chemical vapor deposition method,
(2) vacuum evaporation method,
(3) sputtering method, and
(4) coating method.

Also, there is a strong demand for conductive powder to give conductivity to paints, plastics, fibers, etc., and for example, in Japanese Patent Kokai (Laid-open) No. 77623/1986, a method is proposed in which titanium oxide-tin oxide type composite conductive powder is produced by mixing prescribed quantities of stannous oxalate and antimony chloride with titanium oxide and baking the mixture.

All of the above-mentioned methods (1)–(3) use complicated apparatus and are inferior in operability. In addition, they usually necessitate an etching step after film formation, to form a pattern.

In the method (4) also, when using an inorganic salt such as $SnCl_4$ for example, since hydrogen chloride or other chloride gases are generated upon heat decomposition, severe corrosion of the apparatus takes place. Also, the chlorine remaining in the film may impair conductivity. There are also methods using organic acid salts such as octyl acid tin salt or an organic complex. But in these methods, there are problems such that the uniformity of the film is impaired upon heat decomposition or gelation of the coating liquid takes place. Moreover, they have defects such that the formed film is uneven and cloudy, and is liable to become damaged.

By the method of the above-mentioned Japanese Patent Kokai, it is impossible to cover the surface of titanium oxide with tin oxide, so that not only is the conductivity insufficient but also the performance shows great fluctuation.

Taking the above-mentioned problems of the prior art into account, we carried on further studies, and as a result, we attained the present invention.

The object of the present invention is to provide a novel tin compound which has no restriction or problem on the apparatus, has high applicability, and can finally form tin oxide having excellent transparency and conductivity, in an industrially advantageous manner, and to provide products having a uniform tin oxide film formed on a substrate of any form such as powder form, film form, fiber form, etc. and therefore provides excellent conductivity.

SUMMARY OF THE INVENTION

The above-mentioned object of the present invention is attained by the stannic acid anhydride shown by the structural formula below:

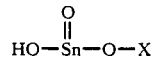

wherein X represents

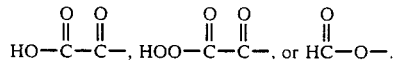

and by conductive products covered with tin oxide produced by baking a substrate of which the surface is coated or impregnated with a water-soluble reaction product of a tin carboxylate with a peroxide (a reaction product such as the above-mentioned stannic acid anhydride).

DETAILED DESCRIPTION OF THE INVENTION

As the carboxylates used in the present invention there may be mentioned for example, stannous formate, stannous acetate, stannous oxalate, stannous tartrate, etc. However, for the attainment of the present invention, stannous oxalate is preferable.

As the peroxide, any may be used as far as it can form a transparent aqueous solution of a tin compound by reacting with the tin carboxylate. For example there may be mentioned $H_2O_2$; alkali-metal peroxides such as $Li_2O_2$, $Na_2O_2$, $K_2O_2$, $Rb_2O_2$, $Cs_2O_2$, etc.; salts of alkali-metals or ammonium of peroxoacids such as $HNO_4$, $H_3PO_5$, $H_4P_2O_8$, $H_2SO_5$, $H_2S_2O_8$, etc.; hydroperoxides such as t-butylhydroperoxide, dimethylbenzylhydroperoxide, etc.; peroxides such as di(3-carboxypropanoyl)peroxide, sec-butanoyl-t-butylperoxide, acetyl t-butylperoxide, etc. Incidentally, when using alkali-metal peroxides or salts of peroxoacids, remaining alkali-metal may impair conductivity, so that $H_2O_2$ and organic peroxides such as hydroperoxides and peroxides are preferable.

There is no restriction as to the quantity of peroxide used as far as it is able to form a transparent aqueous solution of the tin compound by reacting with a tin carboxylate. For example, in the case of using $H_2O_2$ as the peroxide, when the quantity is set at more than 1.5 mol, preferably in the range of 1.6 to 2.2 mol for 1 mol of said tin salt, it is possible to further elevate the uniformity and conductivity of the finally obtained tin oxide coat.

As the aqueous medium, water is usually used, but an amount of water-miscible organic solvent may be used together in a range in which a viscosity rise or gelation of the reaction-produced solution will not occur.

The method of producing the aqueous solution is to add a tin carboxylate to an aqueous medium under stirring, and then add a prescribed quantity of hydrogen peroxide to make them react.

In order to further elevate the conductivity of the finally obtained tin oxide, it is preferable to make a dopant coexist in the reaction system in the ratio of 0.01 to 0.6 mol, preferably 0.03 to 0.5 mol for one mol of the tin carboxylate. Among such dopants may be mentioned compounds containing elements of Group Ib such as Cu, Ag, Au; those of Group IIb such as Cd; those of Group IIa such as Ce, Eu; those of Group VIa such as V, Nb, Ta; those of Group Vb such as As, Sb, Bi; those of Group VIa such as Cr, Mo, W; those of Group VIIa such as Re; those of Group VIII such as Ru, Rh, Pd, Os, Ir, Pt; and fluorine. Among others, compounds containing elements selected from Groups Ib, Va, Vb, VIa, VIII Groups and fluorine are preferable. Especially, coexistence of antimony oxides such as $Sb_2O_3$, $Sb_2O_4$, $Sb_6O_{13}$, etc. or fluorine compounds such as $SnF_2$, $NH_4F$ in the reaction system makes it possible to form a uniform reaction-produced transparent aqueous solution, and finally makes it possible to provide tin oxide having very good conductivity. Therefore such coexistence is desirable.

Even if the reaction is initiated at room temperature, there are cases where boiling may take place by the reaction heat. Therefore, when the reaction is conducted at a temperature below the boiling point, it is desirable that the concentration of the tin carboxylate should be determined generally below 20 weight %, preferably below 18 weight %.

In this way, a transparent aqueous solution of the tin compound can be obtained in a reaction time usually from 5 to 50 minutes. The aqueous solution without any treatment, or after suitable concentration, is baked to produced conductive tin oxide; or the solution is coated on or impregnated into the surface of a substrate and is baked to produce a conductive produce covered with tin oxide.

The baking conditions employed are generally temperatures from 400° C. to 1000° C., preferably from 500° C. to 800° C., for 0.5 to 5 hours, preferably for 1 to 3 hours.

Incidentally, any substrate can be used as far as it can withstand the conditions of baking.

Such substrates include for example, oxides such as zinc white, titanium oxide, antimony white, black iron oxide, red iron oxide, red lead, chromium oxide; sulfides such as lithopone, zinc sulfide, cadmium yellow; sulfates such as barium sulfate, gypsum, lead sulfate; carbonates such as barium carbonate, calcium carbonate powder, white lead; hydroxides such as alumina white; chromates such as chrome yellow, zinc yellow, barium chromate; metal powder such as zinc powder, aluminum powder; inorganic powder such as carbon black, glass beads, glass flake, mica, glaze; inorganic fibers such as carbon fiber, alumina fiber, glass fiber, rock wool, asbestos; ceramic shaped bodies such as tile, insulator, yarn guide; and inorganic products of any optional shape such as film, board, porous body, etc.

As regards the quantity of coating or impregnation, there is no restriction as far as conductive products covered with tin oxide can be obtained. For example, in the case where the substrate is an inorganic powder, it is proper to regulate the quantity of coating or impregnation of the water-soluble reaction product so that the covering quantity of tin dioxide will be generally from 5 to 40% based on the weight of the substrate.

When stannous oxalate selected as tin carboxylate and $H_2O_2$ as peroxide are reacted in the ratio of about 1:1 (molar ratio) while regulating the temperature below about 50° C., preferably between 5° to 45° C. under cooling from outside, it is possible to produce oxalic acid stannic acid anhydride which corresponds to the above-mentioned structural formula in which X is

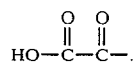

In the same way as above except that the molar ratio of the two is 1:2, it is possible to produce monoperoxalic acid stannic acid anhydride of which X in the structural formula is

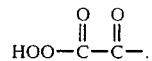

Also, by reacting stannous oxalate with $H_2O_2$ in the ratio of about 1:2 (molar ratio) at a temperature above about 70° C., preferably between 80° and 100° C., it is possible to produce performic acid stannic acid anhydride, of which X in the structural formula is

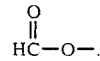

Incidentally, as the method of isolating oxalic acid stannic acid anhydride or peroxalic acid stannic acid anhydride, freeze drying is recommended, since if drying is conducted at a temperature above 70° C. for example, a mixture of complicated compounds is produced as a by-product.

As mentioned above, the novel stannic acid anhydride of the present invention makes it possible to form tin oxide of excellent transparency and conductivity, in any optional form such as powder, film or fiber form, without problems of using a complicated apparatus, or inferior operability.

Also, according to the present invention, by baking a substrate of which the surface is coated or impregnated with the water-soluble reaction product, a uniform tin oxide film is formed on the surface of the substrate, and thus a product of excellent conductivity is provided in an industrially advantageous manner, while the shape of the substrate is utilized as it is.

Thus, the tin oxide and conductive products covered with tin oxide are widely used for various purposes not only as fillers, paints, additives for electrostatic recording paper, films, fibers, etc. in which conductivity and electromagnetic wave shielding properties are especially demanded, but also in transparent heating elements, gas sensors, infrared reflexing films, lithium ion selective adsorbing agents, catalysts, flame-retardants, etc.

EXAMPLES OF THE INVENTION

The present invention will be explained by way of Examples in the following.

The bulk density and the resistivity (Ω.cm) were measured as follows: A sample of 10 g is packed into a cell (inner diameter: 20.5 mm; length: 50 mm), and the compressed height h (mm), by an electode piston (inner diameter: 20 mm; length: 60 mm) under a load of 1 t/cm², and the electric resistance R (Ω) using a four-probe ohm meter (3224 type) produced by Hioki Denki Co. Ltd., were measured.

EXAMPLE 1

190 g stannous oxalate (Sn$_2$O$_4$) was added to 1 liter of water, and while the reaction temperature was regulated at a temperature below 40° C. in an ice bath, 90 g aqueous 35 weight % H$_2$O$_2$ solution was added under stirring. The mixture was reacted for 30 minutes to produce a transparent aqueous solution (a) of oxalic acid stannic acid anhydride.

This transparent aqueous solution (a) showed a very low pH 0.6 and showed a two stage dissociation by potentiometric titration. From this, it is apparent that there are two kinds of acid functional groups in the molecule of the resulting product and one of them has a structure showing a strong acidity comparable to sulfuric acid, and the generation of oxalic acid stannic acid anhydride was confirmed.

Crystals obtained by freeze-drying the transparent aqueous solution (a) were soluble in both water and methanol.

About 0.3 ml of the transparent aqueous solution (a) diluted with about 0.3 ml heavy water was measured for $^{13}$C-NMR. With TMS (tetramethylsilane) used as the external standard, a sharp single line was observed at 160.9 ppm, and the UV spectrum had absorption maxima in the vicinity of 230, 260 and 300 nm, which correspond to the absorption maximum values of tin oxalate, oxalic acid, and meta stannic acid. From this fact, it is considered that there exists an equilibrium condition due to intramolecular rearrangement between the product (a1) of the present invention and the compound (a2) of the following structure.

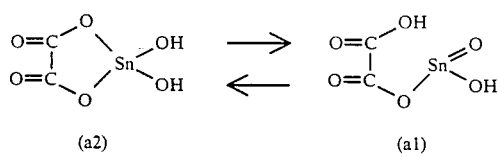

(a2)　　　　　　　(a1)

In the same way as above except that 0.1 mol Sb$_2$O$_3$ for one mol of SnC$_2$O$_4$ was added together with SnC$_2$O$_4$, a transparent aqueous solution (b) was obtained.

After spray-drying the transparent aqueous solutions (a and b), they were ground with a ball mill into powders having an average particle diameter of about 5μ. These powders were baked in the atmosphere at 500° C. for 3 hours to produce two kinds of tin oxide powders (A and B).

The resistivity was obtained, and the results are shown in Table 1 below:

TABLE 1

| Sample | Bulk density (g/ml) | Resistivity (Ω · cm) |
| --- | --- | --- |
| A | 2.4 | 3 × 10$^2$ |
| B | 2.4 | 7 × 10$^{-1}$ |

EXAMPLE 2

To one liter of water was added 210 g SnC$_2$O$_4$. While regulating the reaction temperature below 40° in an ice bath, 200 g aqueous 35 weight % H$_2$O$_2$ solution was added under stirring, and the mixture was reacted for 30 minutes to obtain a transparent aqueous solution (c) of monoperoxalic acid stannic acid anhydride.

The pH of this transparent aqueous solution (c) showed a very low pH of 0.8, and showed one stage dissociation by potentiometric titration. From this fact, it is apparent that the solution has a structure comparable to sulfuric acid.

About 0.3 ml of the transparent aqueous solution (c) diluted with about 0.3 ml heavy water was measured for $^{13}$C-NMR. With TMS (tetramethylsilane) used as the external standard, a single sharp line was observed at 161.4 ppm. From this, it is considered that there is an equilibrium condition due to intramolecular rearrangement between the compound (c1) of the present invention and the compound (c2) of the following structure:

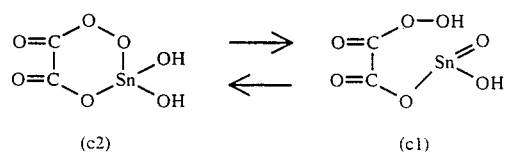

(c2)　　　　　　　(c1)

In the same way as above except that 0.1 mol Sb$_2$O$_3$ for one mol of SnC$_2$O$_4$ was added to the reaction system together with SnC$_2$O$_4$, a transparent aqueous solution (d) was obtained.

After the transparent aqueous solutions (c and d) were spray-dried, they were ground with a ball mill into powders of an average particle diameter of about 5μ, and the powders were baked in the atmosphere at 500° for 3 hours to produce two kinds of tin oxide powders (C and D).

The resistivity was measured, and the results are shown in Table 2 shown below:

TABLE 2

| Sample | Bulk density (g/ml) | Resistivity (Ω · cm) |
| --- | --- | --- |
| C | 2.6 | 2 × 10$^2$ |
| D | 2.6 | 5 × 10$^{-1}$ |

EXAMPLE 3

Two hundred and ten g (210 g) SnC$_2$O$_4$ was added to one liter of water, and 200 g aqueous 35 weight % H$_2$O$_2$ solution was added under stirring. The mixture was reacted at a temperature of from 95° to 97° C. for 30 minutes to obtain a transparent aqueous solution (e) of performic acid stannic acid anhydride. During the reaction, generation of carbon dioxide was observed.

Since the transparent aqueous solution (e) showed a very low pH of 0.8 and showed one stage dissociation by potentiometric titration, it is apparent that the solution has a structure showing a strong acidity comparable to sulfuric acid.

The powder obtained by freeze-drying the transparent aqeuous solution (e) was insoluble in water, and this is considered to have resulted from dehydration condensation which occurred during drying.

About 0.3 ml of the transparent aqueous solution (e) diluted with about 0.3 ml heavy water was measured for $^{13}$C—NMR. With TMS (tetramethylsilane) used as the external standard, a relatively sharp signal and a swelling signal group with a spreading skirt were observed at 162.4 ppm together with a single sharp line at 128 ppm.

From the above-mentioned results, it is considered that peroxalic acid stannic acid anhydride (e1) is generated by the following reaction mechanism, and the compound (e2) also coexists.

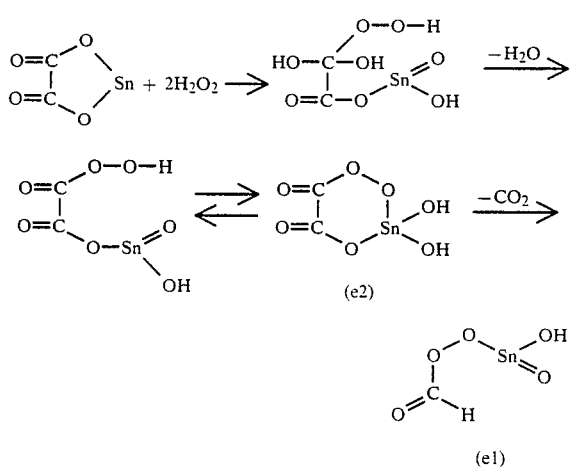

In the same way as above except that 0.1 mol $Sb_2O_3$ for one mol of $SnC_2O_3$ was added together with $SnC_2O_4$, a transparent aqueous solution (f) was obtained.

After the transparent aqueous solutions (e and f) were spray-dried, they were ground with a ball mill into powders of an average particle diameter of about $5\mu$ and the powders were baked in the atmosphere at 500° C. for 3 hours to produce two kinds of tin oxide powders (E and F).

The resistivity was measured, and the results are shown in the following Table 3.

TABLE 3

| Sample | Bulk density (g/ml) | Resistivity ($\Omega \cdot cm$) |
| --- | --- | --- |
| E | 3.4 | $5 \times 10^1$ |
| F | 3.4 | $7 \times 10^{-2}$ |

EXAMPLE 4

The transparent aqueous solution (f) of Example 3 was spinner-coated at 3000 rpm on a quartz glass substrate, and was baked in the atmosphere at 700° C. for 2 hours to produce a transparent conductive film.

The properties of the film are shown in Table 4.

TABLE 4

| Thickness (Å) | Percent transmission (%) | Resistivity* ($\Omega \cdot cm$) | Surface |
| --- | --- | --- | --- |
| 300 | 90 | $6 \times 10^{-2}$ | Smooth, uniform |

*Resistivity was calculated from the electric resistance by four-probe method and the film thickness.

EXAMPLE 5

$SnC_2O_4$ was added to room temperature water, and aqueous 35 weight % $H_2O_2$ solution was added under stirring in the ratio of 2 mols for one mol of $SnC_2O_4$, and the mixture was reacted for 30 minutes at a temperature of about 95° C. generated by reaction heat, to produce a transparent aqueous solution (g) of the reaction product.

A transparent aqueous solution (h) was produced in the same way as above except that 0.1 mol $Sb_2O_3$ for one mol of $SnC_2O_4$ was added together with $SnC_2O_4$. In both cases, the concentration of $SnC_2O_4$ in the reaction system was set at 15 weight %.

To one weight part of each of the thus-produced transparent aqueous solutions (g and h), 4 weight parts of titanium oxide (TA-300, particle diameter $0.3\mu$, produced by Fuji Titan Co.), glass beads (particle diameter $13\mu$, produced by Toshiba Glass Co.), and mica (fine powder of white mica, particle diamter $1\mu$) were added respectively. Then, by drying, the water-soluble reaction products were fixed on the surface of substrates. Incidentally, adhesion between the powder particles of the substrate was not observed.

Then the substrates were baked in the atmosphere at 500° C. for 3 hours to produce 6 kinds of samples to be tested.

The resistivity was measured, and the results are shown in Table 5.

TABLE 5

| Sample | Kind of transparent aqueous solution | Kind of substrate | Resistivity ($\Omega \cdot cm$) |
| --- | --- | --- | --- |
| G1 | g | Titanium oxide | $7 \times 10^4$ |
| G2 | g | Glass beads | $7 \times 10^4$ |
| G3 | g | Mica | $9 \times 10^4$ |
| H1 | h | Titanium oxide | $4 \times 10^{-1}$ |
| H2 | h | Glass beads | $4 \times 10^{-1}$ |
| H3 | h | Mica | $3 \times 10^{-1}$ |

From the above Table, it is clearly understood that the products of the present invention, especially those combined with the dopant, have excellent conductivity.

EXAMPLE 6

Two kinds of samples for testing (H4 and H5) were produced in the same way as Example 5 H1 except that glass fiber (diameter $15\mu$; length 3 mm) and asbestos (Canadian chrysotile No. 1) were used as the substrates. The results are shown in Table 6.

TABLE 6

| Sample | Kind of substrate | Resistivity ($\Omega \cdot cm$) |
| --- | --- | --- |
| H4 | Glass fiber | $3 \times 10^{-1}$ |
| H5 | Asbestos | $5 \times 10^{-1}$ |

EXAMPLE 7

A sample for testing (H6) was produced in the same way as Example 5 except that the transparent aqueous solution (h) was fixed by spraying on a tile (unglazed tile, produced by Yodogawa Sangyo Co.).

The surface resistance was measured by a surface resistance tester (MCP tester produced by Mitsubishi Petrochemical Co. Ltd.). The result was 500 $\Omega/cm^2$.

EXAMPLE 8

A sample for testing (H7) was produced in the same way as Example 5 H1 except that t-butyl hydroperoxide was used instead of $H_2O_2$ and 0.4 mol $NH_4F$ was used instead of $Sb_2O_3$.

The sample showed an excellent conductivity, with the resistivity being $7 \times 10^{-1} \Omega \cdot cm$.

EXAMPLE 9

Transparent aqueous solutions (i and j) were produced in the same way as Example 5 except that 1.5 mol di(3-carboxy propanoyl) peroxide was used instead of 2 mol t-butyl hydroperoxide and except that 0.3 mol $NH_4F$ for one mol of $SnC_2O_4$ was used, and in the same way as Example 3, tin oxide powders (I and J) were produced.

The resistivity was measured and the results are shown in Table 7.
TABLE 7
| Sample name | Resistivity (Ω · cm) |
|---|---|
| I | $7.4 \times 10^1$ |
| J | $8.9 \times 10^{-2}$ |
What is claimed is:
1. Stannic acid anhydride shown in the following structural formula:
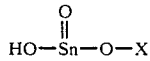
wherein X represents
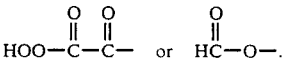
* * * * *